United States Patent [19]

Noiles

[11] 4,351,466

[45] Sep. 28, 1982

[54] DISPOSABLE INSTRUMENT FOR SURGICAL FASTENING

[75] Inventor: Douglas G. Noiles, New Canaan, Conn.

[73] Assignee: United States Surgical Corporation, Norwalk, Conn.

[21] Appl. No.: 197,614

[22] Filed: Oct. 16, 1980

[51] Int. Cl.³ .................. A61B 17/04; A61B 17/11
[52] U.S. Cl. .................................. 227/8; 227/19; 227/DIG. 1; 128/334 R
[58] Field of Search ............... 128/334 R, 326, 325; 227/19, DIG. 1, 8; 222/391

[56] References Cited

U.S. PATENT DOCUMENTS

| | | | |
|---|---|---|---|
| 2,891,250 | 6/1959 | Hirata | 1/50 |
| 2,940,451 | 6/1960 | Vogelfanger et al. | 128/334 |
| 2,965,900 | 12/1960 | Inokouchi | 1/50 |
| 3,080,564 | 3/1963 | Strekopitov et al. | 1/50 |
| 3,082,426 | 3/1963 | Miles | 1/349 |
| 3,144,654 | 8/1964 | Mallina et al. | 1/50 |
| 3,176,896 | 4/1965 | Mallina | 227/19 |
| 3,191,842 | 6/1965 | Fischer et al. | 227/155 |
| 3,193,165 | 7/1965 | Akhalaya et al. | 227/8 |
| 3,225,996 | 12/1965 | Mallina | 227/137 |
| 3,252,643 | 5/1966 | Strekopytov et al. | 277/109 |
| 3,269,630 | 8/1966 | Fleischer | 227/107 |
| 3,269,631 | 8/1966 | Takaro | 227/144 |
| 3,388,847 | 6/1968 | Kasulin et al. | 227/19 |
| 3,494,533 | 2/1970 | Green et al. | 227/19 |
| 3,518,993 | 7/1970 | Blake | 128/321 |
| 3,552,626 | 1/1971 | Astafiev et al. | 227/76 |
| 3,589,589 | 6/1971 | Akopov | 227/153 |
| 3,593,903 | 7/1971 | Astafiev et al. | 227/76 |
| 3,638,652 | 2/1972 | Kelley | 128/305 |
| 3,687,138 | 8/1972 | Jarvik | 128/326 |
| 3,692,224 | 9/1972 | Astafiev et al. | 227/19 |
| 3,790,057 | 2/1974 | Razgulov et al. | 227/19 |
| 3,795,034 | 3/1974 | Strekopytov et al. | 29/212 D |
| 3,836,061 | 9/1974 | Grunwald | 227/155 |
| 3,935,981 | 2/1976 | Akopov et al. | 227/19 |
| 4,152,920 | 5/1979 | Green | 128/325 X |
| 4,166,466 | 9/1979 | Jarvik | 128/325 |
| 4,207,898 | 6/1980 | Becht | 128/305 |

FOREIGN PATENT DOCUMENTS 1057729  5/1959  Fed. Rep. of Germany .
587678   1/1959  Italy .
1241577  8/1971  United Kingdom .

OTHER PUBLICATIONS

Japanese Brochure of Yufu Medical, Inc. (prior to Feb. 8, 1979).
Unidentified Japanese Brochure (no date).
"Information Booklet for Auto Suture ® Model EEA Surgical Stapling Instrument and Disposable Fastening Units" (1/79).

Primary Examiner—Michael H. Thaler
Attorney, Agent, or Firm—Robert R. Jackson

[57] ABSTRACT

A disposable surgical stapler is provided which comprises:

a tubular housing having an axial bore and an axial slot which extends through its tubular wall;

a tubular pusher axially located within the bore of the housing and adapted to move distally and proximally within the bore; the pusher having an axial slot extending through its tubular wall;

a central rod axially located within the pusher and adapted to move distally and proximally within the pusher; the central rod having an axial groove in its lateral surface;

a handle pivotally mounted on the tubular wall of the housing; one part of the handle being positioned within the slot in the housing and within the slot in the pusher; and being adapted to move distally against the distal end of the slot in the pusher to move the pusher distally;

an anvil mounted in a predetermined indexed orientation on the distal end of said center rod;

a staple carrying assembly mounted on the distal end of said housing;

the groove in the central rod being located, so that when the anvil and the staple carrying assembly are properly spaced apart for fastening tissue between them: one part of the handle can move medially and distally into the groove of said central rod and distally against the distal end of the slot of the pusher to move the pusher distally within the bore of the housing against the proximal end of the staple carrying assembly to activate the staple carrying assembly.

6 Claims, 19 Drawing Figures

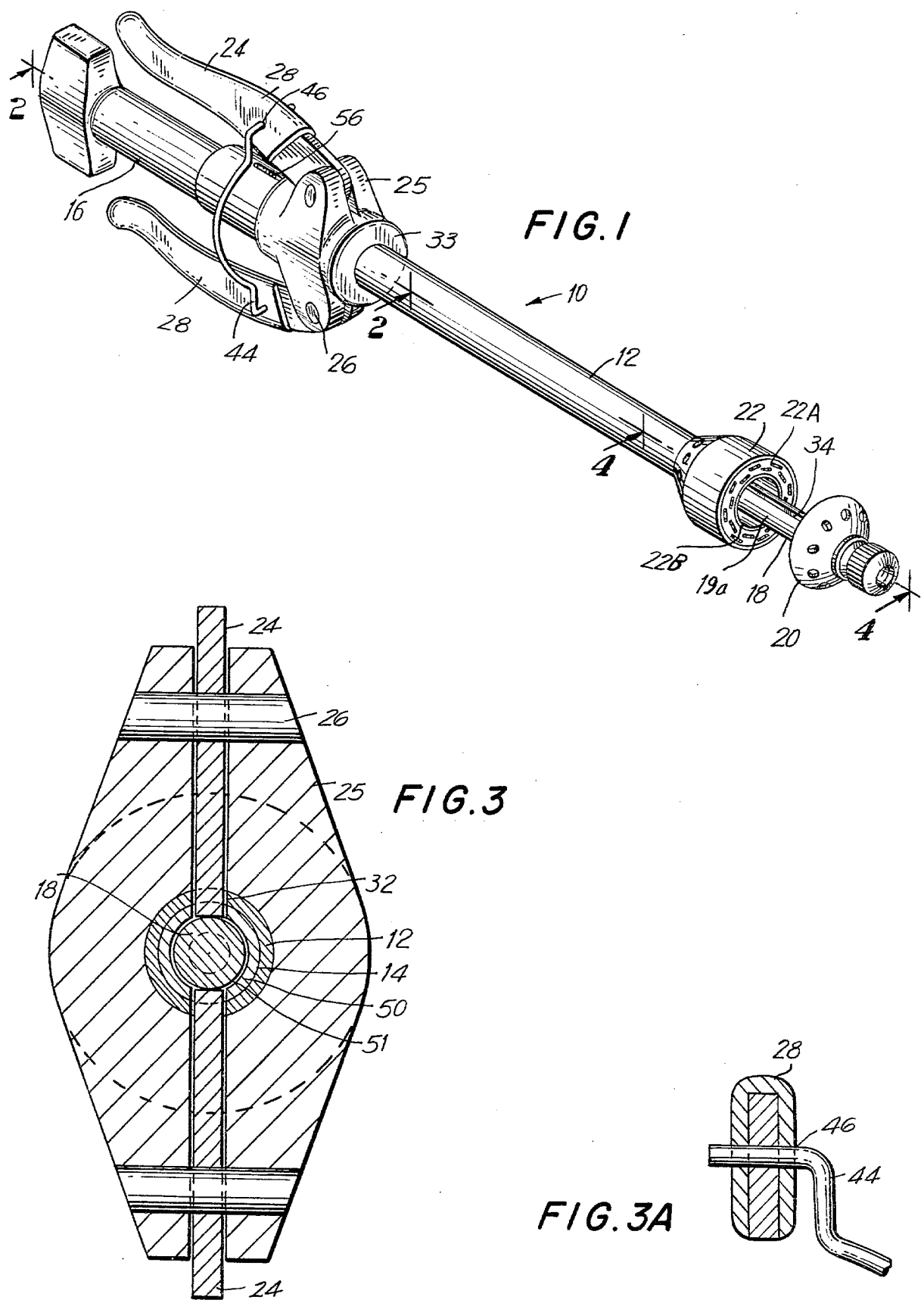

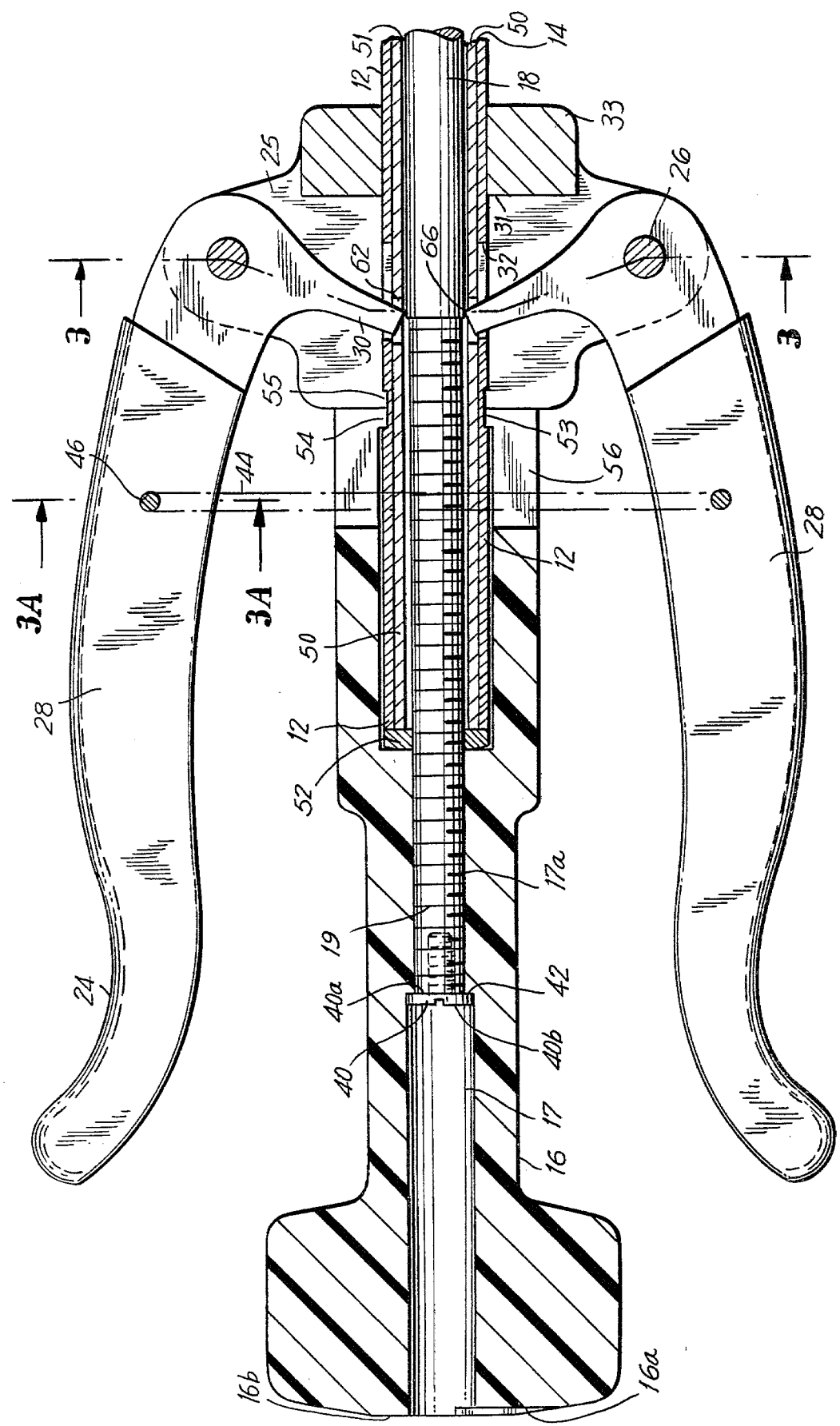

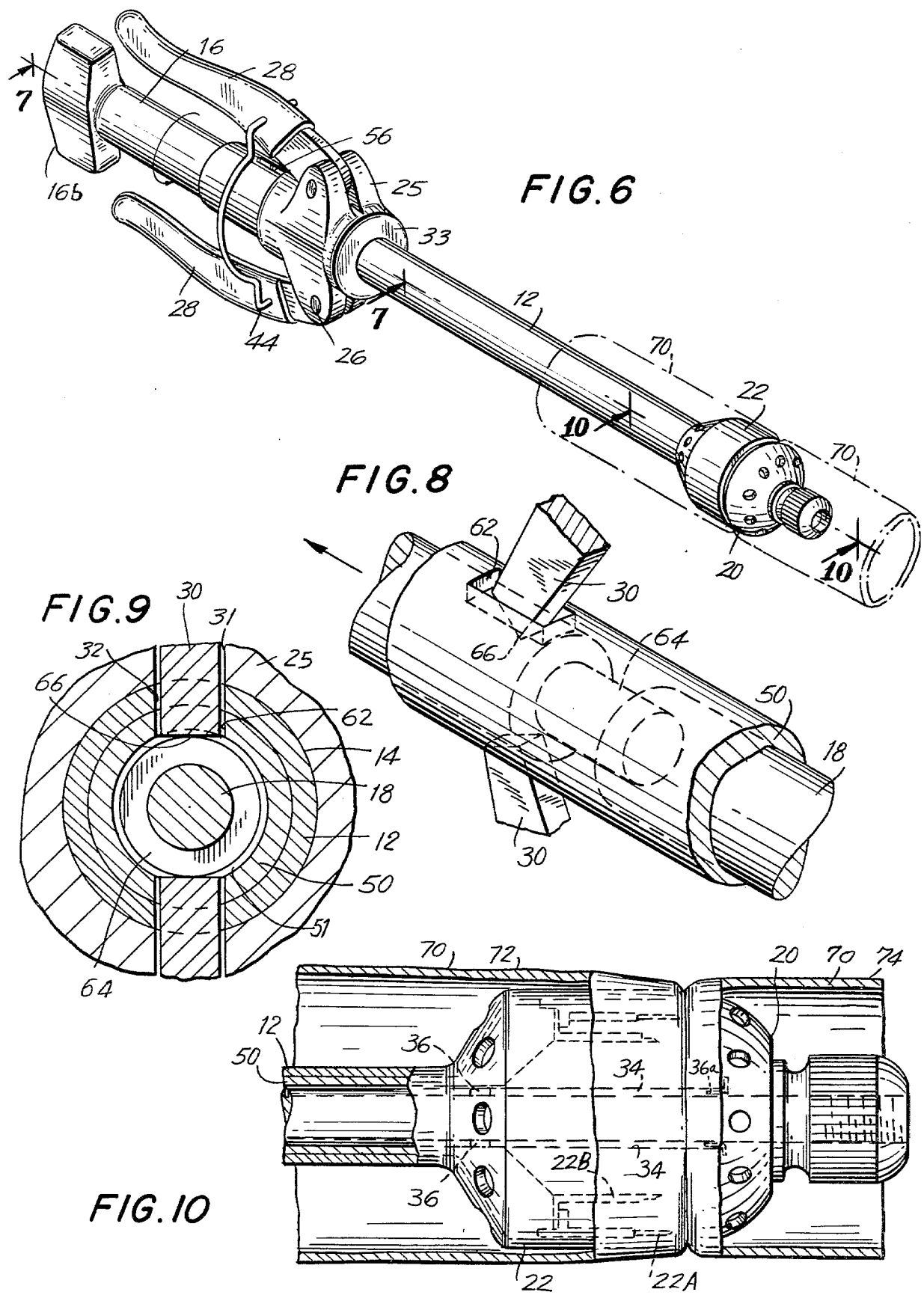

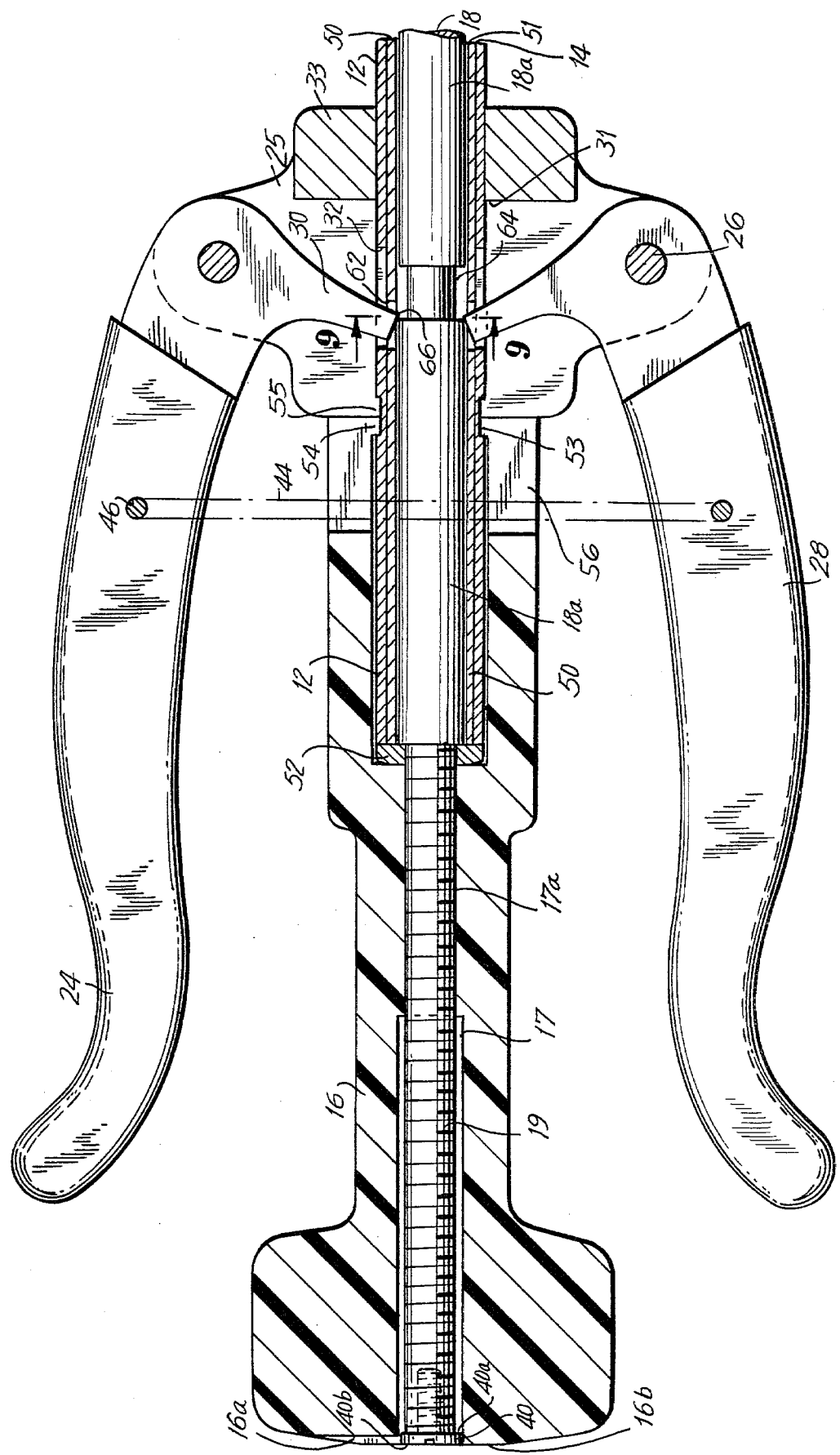

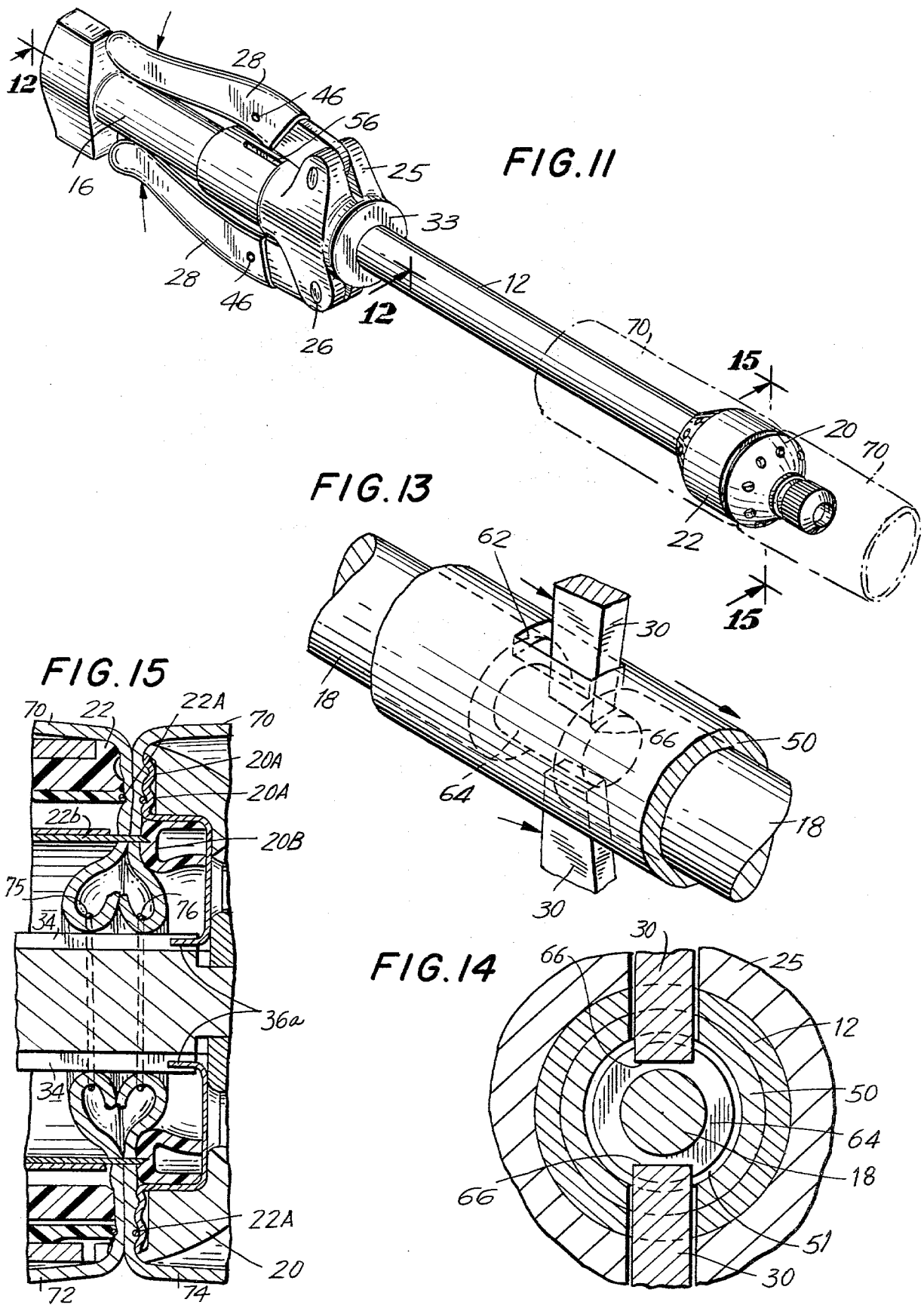

DISPOSABLE INSTRUMENT FOR SURGICAL FASTENING

BACKGROUND OF THE INVENTION

This invention relates to a relatively simple and inexpensive instrument for surgical fastening (e.g., surgical stapling) which can be discarded after it has been used. This invention particularly relates to a disposable instrument for circular surgical fastening of hollow body organs (e.g., sections of the colon or esophagus) so as to effect an anastomosis.

Instruments are known for the circular surgical fastening of hollow body organs. See, for example, U.S. Pat. Nos. 2,940,451, 2,965,900, 3,082,426, 3,144,654, 3,176,896, 3,191,842, 3,193,165, 3,225,996, 3,269,631, 3,388,847, 3,552,626, 3,593,903, and 3,638,652. From U.S. patent application, Ser. No. 967,421, filed Dec. 7, 1978, entitled "Instrument For Circular Surgical Stapling Of Hollow Body Organs And Disposable Cartridge Therefor", an instrument for circular surgical fastening is known which can have a disposable cartridge assembly, containing surgical staples and a knife, mounted on it before use and removed from it after use.

However, all such instruments have been designed to be made from relatively expensive, corrosion and wear resistant, metal parts. Such instruments have not been adapted to be made from relatively inexpensive materials (e.g., plastic). Furthermore, many of such instruments have been designed with relatively complex mechanisms. Therefore, it has not been considered practical to dispose of such instruments after one use. This has meant that such instruments have had to be cleaned, sterilized and stored after each use. Also, significant capital investments have had to be made by hospitals in such instruments. Further, such instruments, through mishandling or wear, have required, from time to time, costly servicing and repair.

Thus, a surgical fastening instrument has been sought which can be made, at least in part, from relatively inexpensive materials (e.g., plastic, aluminum, and plated low carbon steel) and which can be discarded in its entirety after use.

SUMMARY OF THE INVENTION

In accordance with this invention, a disposable surgical fastening instrument is provided, which comprises:

(a) a tubular housing having an axial bore and an axial slot which extends through its tubular wall;

(b) a tubular pusher axially located within the bore of said housing and adapted to move distally and proximally within the bore; said pusher having an axial slot extending through its tubular wall;

(c) a central rod axially located within said pusher and adapted to move distally and proximally within said pusher; said central rod having an axial groove in its lateral surface;

(d) means, located at the proximal end of said housing, for moving said central rod distally and proximally within said pusher;

(e) a handle pivotally mounted on the tubular wall of said housing; the pivotal mounting of said handle being laterally spaced from the tubular wall of said housing; a first part of said handle being located on the side of the pivotal mounting remote from said housing and being adapted to move about the pivotal mounting towards said housing; a second part of said handle being located on the other side of the pivotal mounting, adjacent to said housing, and being positioned within the slot in said housing and within the slot in said pusher; the second part of said handle being adapted to move distally against the distal end of the slot in said pusher to move said pusher distally within the bore of said housing upon movement of the first part of said handle towards said housing; the end of the second part of said handle, remote from the pivotal mounting, being spaced from the pivotal mounting by a distance greater than the lateral distance between the pivotal mounting and the lateral surface of said center rod;

(f) an anvil mounted in a predetermined indexed orientation on the distal end of said center rod;

(g) a staple carrying assembly mounted in a predetermined indexed orientation on the distal end of said housing between said anvil and the distal end of said pusher; said staple carrying assembly being activated by distal movement of said pusher against the proximal end of said staple carrying assembly, so that staples are urged distally against said anvil; and (h) means for determining that the axial position of the distal end of said central rod relative to the distal end of said housing is such that said anvil and said staple carrying assembly are properly spaced apart for fastening tissue between them;

the groove in said central rod being located, so that when said anvil and said staple carrying assembly are properly spaced apart for fastening tissue between them: (1) at least a portion of the slot in said pusher is laterally aligned with at least a portion of the groove in said central rod; and (2) the end of the second part of said handle, remote from the pivotal mounting, can move medially and distally into the groove of said central rod and the second part of said handle can move distally against the distal end of the slot of said pusher to move said pusher distally within the bore of said housing against the proximal end of said staple carrying assembly to activate said staple carrying assembly.

Major parts of this instrument can be made of relatively inexpensive materials (e.g., plastic, aluminum, and plated low carbon steel). As a result, the instrument can suitably be discarded after use.

BRIEF DESCRIPTION OF THE DRAWINGS

FIG. 1 is a perspective view of one embodiment of the surgical fastening instrument of this invention. FIG. 1 shows the instrument with its axially movable, central rod extending as far distally as it will go. In FIG. 1, an anvil assembly, mounted on the distal end of the central rod, is spaced from a staple carrying assembly which is integral with the distal end of the housing of the instrument. A removable, wire safety stop is placed in holes in the handles as an added safety feature to prevent inadvertent movement of the handles.

FIG. 2 is a partial sectional view taken along line 2—2 in FIG. 1. FIG. 2 shows the housing, central rod, wing nut, pusher, and handlers of the instrument.

FIG. 3 is a partial sectional view taken along line 3—3 in FIG. 2.

FIG. 3a is a sectional view taken along line 3a—3a in FIG. 2.

FIG. 4 shows the instrument's distal end inserted into sections of a hollow body organ before clamping and then fastening them together.

FIG. 6 is a perspective view of the instrument of FIG. 1 showing the anvil assembly and staple carrying assembly clamping sections of a hollow body organ together before the sections are fastened together.

FIG. 7 is a partial sectional view, taken along line 7—7 in FIG. 6. FIG. 7 shows the housing, central rod, handles, pusher and wing nut of the instrument prior to moving the handles towards the housing to urge the pusher distally so as to activate the staple carrying assembly.

FIG. 8 is a partial perspective view of portions of the handle, pusher and central rod of the instrument of FIG. 1 in the positions shown in FIG. 5.

FIG. 9 is a sectional view taken along line 9—9 in FIG. 7.

FIG. 10 is a sectional view, similar to FIG. 4, taken along line 10—10 in FIG. 6. FIG. 10 shows the anvil and staple carrying assemblies of the instrument of FIG. 1 clamping sections of a hollow body organ together before the staple carrying assembly is activated by distal movement of the pusher to fasten the section together.

FIG. 11 is a perspective view of the instrument of FIG. 1 showing the instrument after the handles have been moved towards the housing to activate the staple carrying assembly to fasten the tissue between the anvil and staple carrying assemblies.

FIG. 13 is a partial perspective view of portions of the handles, pusher and central rod of the instrument of FIG. 1 in the positions shown in FIG. 12.

FIG. 14 is a sectional view taken along line 14—14 in FIG. 12.

FIG. 15 is a sectional view taken along line 15—15 in FIG. 11. FIG. 15 shows the staple carrying and anvil assemblies after the staple carrying assembly has been activated and sections of a hollow body organ have been fastened together by the staple carrying and anvil assemblies.

In FIG. 16, a locking cam ring, rotatably mounted about the housing and between the handles, has replaced the wire safety stop shown in FIG. 1.

DETAILED DESCRIPTION OF THE PREFERRED EMBODIMENT

Figure 4:
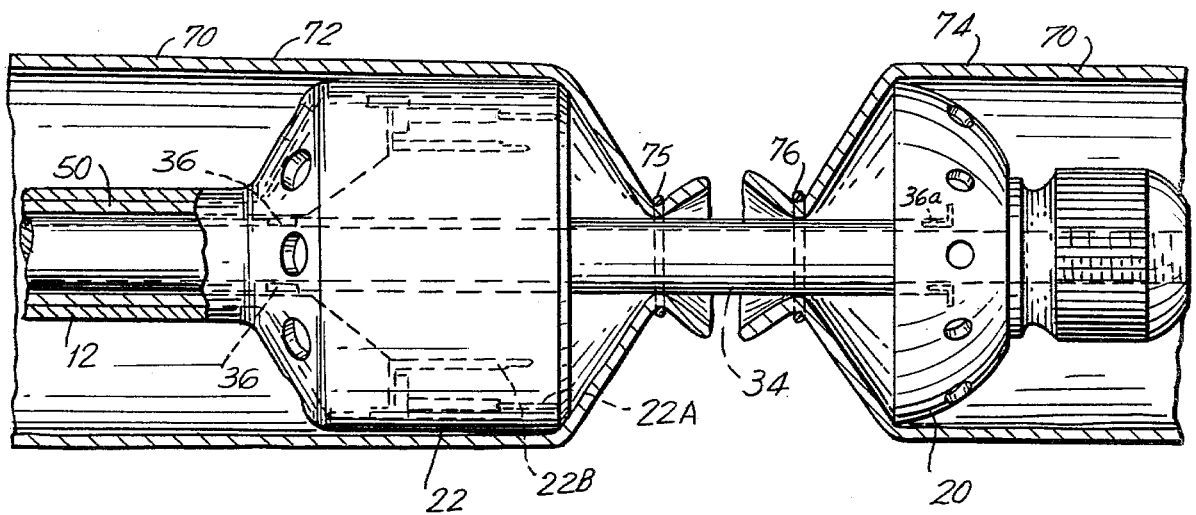
FIG. 4 is a sectional view of the distal end of the instrument, taken along line 4—4 in FIG. 1.

Although the principles of this invention are applicable to other surgical fastening instruments, the invention will be fully understood from an explanation of its application to a surgical stapler for performing an anastomosis of a hollow body organ.

Shown in FIGS. 1 to 15 is one embodiment, generally 10, of a surgical fastening instrument of this invention. The instrument 10 includes an elongated hollow tubular body or housing 12 having an axial bore 14 therethrough. The rear or proximal end of the instrument 10, proximally of the housing 12, comprises a wing nut 16 having an axial bore 17 therethrough. The bores 14 and 17 of the housing 12 and wing nut 16 are coaxial. The wing nut 16 is preferably a one-piece plastic (e.g., polycarbonate or ABS) member, and the housing 12 is preferably a one-piece metal (e.g., aluminum) member. Projecting from the forward or distal end of the housing 12 is a central rod 18. The central rod 18 is axially located within the bore 14 of the housing 12 and is adapted to move distally and proximally within the bore 14 of the housing. Central rod 18 extends distally of, and terminates at a substantial distance from, the distal end of the housing 12. The central rod 18 also extends proximally of the housing 12. The central rod 18 extends into, and is axially located within, the bore 17 of the wing nut 16. The central rod 18 is adapted to move distally and proximally within the bore 17 of the wing nut 16.

The central rod 18 is subject to considerable forces during the clamping, stapling and cutting of tissue with the instrument 10 of this invention. The central rod 18 therefore has to be made from a material that is able to withstand relatively heavy loads (e.g., 500 pounds). Therefore, it is preferred that the central rod 18 be made of a metal (e.g., plated low carbon steel).

On the distal end of the central rod 18 is an anvil assembly, generally 20. On the distal end of the housing 12, proximally of the anvil assembly 20, is a staple carrying assembly, generally 22. Both the anvil assembly 20 and staple carrying assembly 22 can be integral with the instrument 10. If desired, the anvil assembly 20, the staple carrying assembly 22 or both can also be separate pieces that are adapted to be securely attached to the instrument 10 in a predetermined indexed orientation by the user of the instrument in a manner known to those skilled in the art. Preferably, in a disposable instrument 10 of this invention, the staple carrying assembly 22 and the housing 12 are one piece, but the anvil assembly 20 and the central rod 18 are separate pieces with the anvil assembly 20 being adapted to being screwed on, or otherwise securely affixed, to the distal end of the central rod 18 in a predetermined indexed orientation with respect to the staple carrying assembly 22.

The structure and dimensions of the anvil and staple carrying assemblies 20 and 22 are not part of the invention, and any conventional compatible anvil and staple carrying assemblies 20 and 22, such as the anvil and staple carrying assemblies described in U.S. patent application No. 967,421, filed Dec. 7, 1978, entitled "Instrument For Circular Surgical Stapling Of Hollow Body Organs And Disposable Cartridge Therefor", can be suitably utilized. As shown in FIGS. 4, 10 and 15, the anvil assembly 20 of instrument 10 preferably has two concentric annular rows of stapling crimping pockets 20A and an annular knife cutting ring 20B. The staple carrying assembly 22 contains a plurality of surgical staples 22A pointing toward the anvil assembly 20 and arranged in two concentric annular rows. Preferably, the staple carrying assembly 22 also contains an annular knife 22B, concentric with, but inside of, the annular staple array. Each pocket 20A of the anvil assembly 20 is aligned with a respective one end of a staple 22A in the staple carrying assembly 22, and the knife cutting ring 20B of the anvil assembly 20 is aligned with the knife 22B of the staple carrying assembly 22. In the instrument 10 of this invention, distal pressure against the proximal end of the staple carrying assembly 22 activates it, causing its knife 22B to be urged distally into the knife cutting ring 20B of the anvil assembly 20 and causing its staples 22A to be urged distally against, and to be crimped by, the pockets 20A of the anvil assembly.

Projecting laterally from opposite sides of the housing 12 of the instrument 10 are a pair of one-piece handles 24. Each handle 24 is pivotally mounted on the tubular wall of the housing 12 by means of an annular yoke 25 about the lateral surface of the tubular wall of the housing 12. The yoke 25 carries a pair of pivot pins 26, laterally spaced from the tubular wall of the housing 12. Each handle 24 comprises a first handle part 28, located on the side of its pivot pin 26 remote from the housing 12, and a second handle part 30, located on the other side of its pivot pin 26. Each second handle part 30 extends into an axial slot 31 in the yoke 25 and an axial slot 32 in the housing 12. As seen from FIGS. 2, 5, 7 and 12, the slots 31 extend medially through opposite sides of the yoke 25 and extend distally from the proximal end of the yoke to an annular ring 33 adjacent the distal end of the yoke 25. The slots 31 in the yoke 25 permit the second handle parts 30 to move medially and distally into the slots 32 in opposite sides of the housing 12. As also seen from FIGS. 2, 7 and 12, the slots 32 in the housing 12 extend medially through its tubular wall and proximally of the pivot pins 26.

The handles 24 can be made of metal. Preferably, the handles 24 are made from a metal (e.g., plated low carbon steel), and their first handle parts 28 are covered with a plastic.

The dimensions of the handles 24 are not critical. Preferably, the first handle parts 28 are about three to seven times longer than the second handle parts 30, especially about five times longer. Such relative dimensions provide sufficient amplification of the force of the operator of the instrument 10, squeezing with one hand the handles 24 of the instrument 10 together, to obtain clamping, stapling and cutting of tissue with the anvil and staple carrying assemblies 20 and 22 of the instrument 10.

Figure 12:
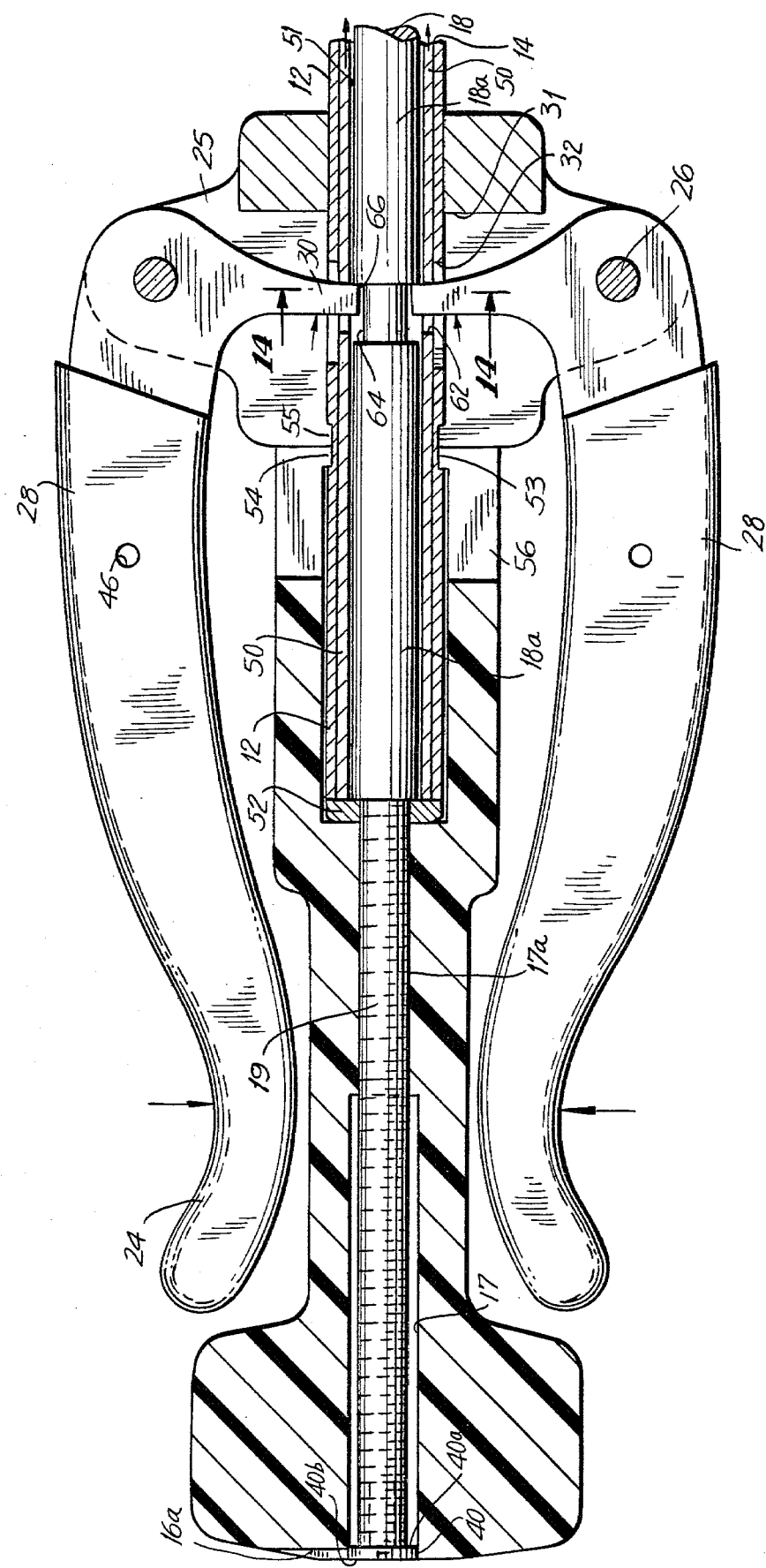
FIG. 12 is a partial sectional view, taken along line 12—12 in FIG. 11, showing the wing nut, housing, handles, pusher and central rod after the handles have been moved toward the housing to urge the pusher distally so as to activate the staple carrying assembly.

As seen from FIGS. 2 and 12, each second handle part 30 preferably forms a right angle with its first handle part 28. However, this angle is not critical.

In accordance with this invention, the location and dimensions of the slots 31 in the yoke 25 and the slots 32 in the housing 12 are not critical. However, the dimensions and locations of the slots 31 and 32 must permit the second handle parts 30 to move distally and medially a substantial distance through the slots 31 and 32 upon movement of the first handle parts 28 towards the wing nut 16 and the housing 12 (within the wing nut 16) without interference from the yoke 25 or the tubular wall of the housing 12. In this regard, each slot 31 and 32 should be somewhat wider than each second handle part 30 and should extend proximally from about the pivot pins 26. Preferably, the proximal end of each slot 32 in the housing 12 extends far enough distally to prevent each second handle part 30 from moving laterally outward of the slot 32 when the first handle parts 28 are moved laterally away from the housing 12 and wing nut 16.

When the wing nut 16 is held in the palm of the hand of the operator of the instrument 10, the first handle parts 28 of the pair of handles 24 can be grasped by the fingers of the operator's hand. The first handle parts 28 also can be pressed towards the wing nut 16 and the housing 12 to make the handles 24 pivot about pivot pins 26. When the handles 24 pivot, the first handle parts 28 move medially towards the wing nut 16 and housing 12, and the second handle parts 30 move medially and distally within the slots 31 and 32 of the yoke 25 and housing 12 unless, as will be described hereinafter, movement of the second handle parts 30 is prevented by portions of the lateral surface 18a of the central rod 18 in accordance with this invention.

Rotation of the wing nut 16 of the instrument 10 can be used to move the central rod 18 either distally or proximally within the axial bore 14 of the housing 12 and within the axial bore 17 of the wing nut 16. This is because a portion 19 of the central rod 18, adjacent its proximal end, is provided with threads which mate with threads on a constricted portion 17a of the axial bore 17 of the wing nut 16 as shown in FIGS. 2, 7 and 12.

Another portion 19a of the central rod 18, adjacent its distal end, has a pair of axial keyways 34 on opposite sides of the central rod 18. A pair of keys 36 is provided on opposite sides of the interior surface of the staple carrying assembly 22 adjacent the central rod 18, and a second pair of keys 36a is provided on opposite sides of the interior surface of the anvil assembly 20 adjacent the central rod 18. The keys 36 and 36a fit into the keyways 34. The fit of the keyways 34 and keys 36 on the staple carrying assembly 22 prevents rotation of the central rod 18 relative to the housing 12 when the wing nut 16 is rotated to move the central rod 18 axially. The fit of the keyways 34 and the keys 36a on the anvil assembly 20 assures that the anvil and staple carrying assemblies 20 and 22 are in a predetermined indexed orientation on the central rod 18 for proper fastening of tissue.

Provided on the proximal end of the central rod 18 is a stop screw 40 which extends laterally of the threaded portion 19 of the central rod 18. The distal surface 40a of the stop screw 40 is adapted to abut against an inwardly projecting shoulder 42 that is located in the bore 17 of the wing nut 16 proximally of the threaded constricted portion 17a of the bore 17 of the wing nut 16. The distal surface 40a of the stop screw 40 and the shoulder 42 serve to restrict distal movement of the central rod 18.

In accordance with this invention, the proximal surface 40b of the stop screw 40 serves as a means for determining that the position of the distal end of the central rod 18, relative to the distal end of the housing 12, is such that the anvil assembly 20 (on the distal end of the central rod 18) and the staple carrying assembly 22 (on the distal end of the housing 12) are properly spaced apart for fastening tissue between them. The length of the central rod 18 and the lengths of the coaxial bores 14 and 17 through the housing 12 and the wing nut 16 are such that, when the proximal surface 40b of the stop screw 40 is flush, i.e., coplanar, with the proximal surface 16a of the wing nut 16, the anvil assembly 20 and the staple carrying assembly 22 are properly spaced apart for fastening tissue between them.

Preferably, a stepped surface 16b is provided on the proximal surface 16a of the wing nut 16 adjacent to, and on one side of, the axial bore 17 in the wing nut 16. In this preferred embodiment, when the proximal surface 40b of the stop screw 40 is flush with the proximal surface 16a of the wing nut 16, the anvil assembly 20 and the staple carrying assembly 22 are properly spaced apart for fastening tissue between them, i.e., are close enough (not too far apart) to obtain what is generally considered effective fastening of tissue. When the proximal surface 40b of the stop screw 40 is flush with the stepped surface 16b of the wing nut 16, the anvil assembly 20 and the staple carrying assembly 22 are as close as is generally considered suitable (not too close) for effective fastening of tissue.

When the proximal surface 40b of the stop screw 40 is flush with the proximal surface 16a of the wing nut 16 or flush with the stepped surface 16b of the wing nut or located between the proximal and stepped surfaces 16a and 16b of the wing nut, the instrument 10 of this invention can be used for surgically fastening tissue between the anvil assembly 20 and the staple carrying assembly 22 as will be discussed hereinafter. Before fastening tissue with the instrument, a wire safety stop 44, shown in FIGS. 1 and 3A, must be removed to free the handles 24. Then, the first handle parts 28 can be squeezed together, towards the wing nut 16 and housing 12. The ends of the wire safety stop 44 are mounted in holes 46 through the first handle parts 28 as an added safety feature to prevent the handles from being moved medially towards the housing 12 until the operator of the instrument 10 is ready to fasten tissue.

As seen from FIGS. 2, 7 and 12, a tubular pusher 50 is provided within the axial bore 14 of the housing 12 of the instrument 10. The pusher 50 is adapted to move both distally and proximally within the bore 14. The distal end of the pusher 50 is particularly adapted to move distally against the proximal end of the staple carrying assembly 22 and into the staple carrying assembly 22 to urge its knife 22B distally into the knife cutting ring 20B of the anvil assembly 20 and to urge its staples 22A distally against the pockets 20A of the anvil assembly to crimp the staples. The pusher 50 is, therefore, subject to considerable forces during the stapling and cutting of tissue with the instrument. Thus, the pusher 50 has to be made from a material that is able to withstand relatively heavy loads (e.g., 400 pounds). It is preferred that the pusher 50 be made of a metal (e.g., plated low carbon steel).

The central rod 18 is located within the axial bore 51 of the pusher 50. The central rod 18 is adapted to move distally and proximally within the bore 51 of the pusher 50. The pusher 50 is located distally of the constricted threaded portion 17a of the axial bore 17 of the wing nut 16. To protect the plastic wing nut 16, about the constricted portion 17a of its axial bore 17, from being harmed by the metal pusher 50 or the metal housing 12, an annular thrust washer 52 is provided about the central rod 18, proximally of the pusher 50 and housing 12.

As seen from FIGS. 2, 7 and 12, an annular groove 53 is provided in the lateral surface of the housing 12 near its proximal end. As also seen from FIGS. 2, 7 and 12, an inwardly extending, annular shoulder 54 is provided on the distal end of the axial bore 17 of the wing nut 16, and an inwardly extending, annular shoulder 55 is provided on the proximal end of the yoke 25. The wing nut shoulder 54 and the yoke shoulder 55 engage the groove 53 in the housing 12, so that the distal end of the wing nut 16 abuts the proximal end of the yoke 25.

To allow the distal end of the wing nut 16 to be expanded temporarily, so that its shoulder 54 can be fit within groove 53 in the housing 12, a pair of axial slots 56 are provided on opposite sides of the wing nut 16. The slots 56 extend proximally from the distal end of the wing nut 16 and extend through the tubular wall of the distal end of the wing nut 16.

The axial slots 31 in the yoke 25, extending proximally from the annular ring 33 to the proximal end of the yoke 25, allow the proximal end of the yoke 25 to be expanded temporarily, so that the shoulder 55 of the yoke 25 can be fit into the groove 53 of the housing 12.

As seen from FIGS. 2, 5, 7 and 12, the pusher 50 has a pair of axial slots 62 on its opposite sides extending through its tubular wall. The width of each slot 62 is somewhat greater than the width of one of the second handle parts 30. The location of the distal end of each slot 62 in the pusher 50 is critical to the proper operation of the instrument 10 as will be described hereinafter. In this regard, the distal end of each slot 62 must be so located that it can be urged distally by a second handle part 30 as the second handle part moves distally and medially when its first handle part 28 is pressed towards the housing 12 and wing nut 16. The distal ends of the slots 62 also must be so located that they can be moved distally a sufficient distance by distal movement of the second handle parts 30, so that the staple carrying assembly 22 is activated by the distal movement of the pusher 50 and the staples 22A and the knife 22B of the staple carrying assembly 22 are urged against the anvil assembly 20 to fasten and cut tissue and the staples 22A are properly crimped by the anvil assembly.

As also seen from FIGS. 5, 7, 8, 12 and 13, a circumferential axial groove 64 is provided in the lateral surface 18a of the central rod 18. The location of the proximal and distal ends of the axial groove 64 and the depth of the groove 64 in the central rod 18 are critical to the proper operation of the instrument 10 of this invention as will be discussed hereinafter. In this regard, the proximal end of the groove 64 in the central rod 18 must be located, so that the end 66 of each second handle part 30, remote from its pivot pin 26, can move medially into the groove 64 without abutting against the lateral surface 18a of the central rod 18, proximally of the groove 64, when the first handle parts 28 are pressed towards the housing 12 and when the proximal surface 40b of the stop screw 40 is flush with, or proximal of, the proximal surface 16a of the wing nut 16. Also, the distal end of the groove 64 must be located, so that the remote end 66 of each second handle part 30 can move distally in the groove 64 without abutting against the distal end of the groove 64 until the staple carrying assembly 22 is activated by distal movement of the pusher 50 (caused by distal movement of the second handle parts 30 against the distal ends of the slots 62 in the pusher 50), so that the staples 22A and knife 22B of the staple carrying assembly 22 are urged against the anvil assembly 20 to fasten and cut tissue and so that the staples are properly crimped by the pockets 20A of the anvil assembly.

Figure 5:
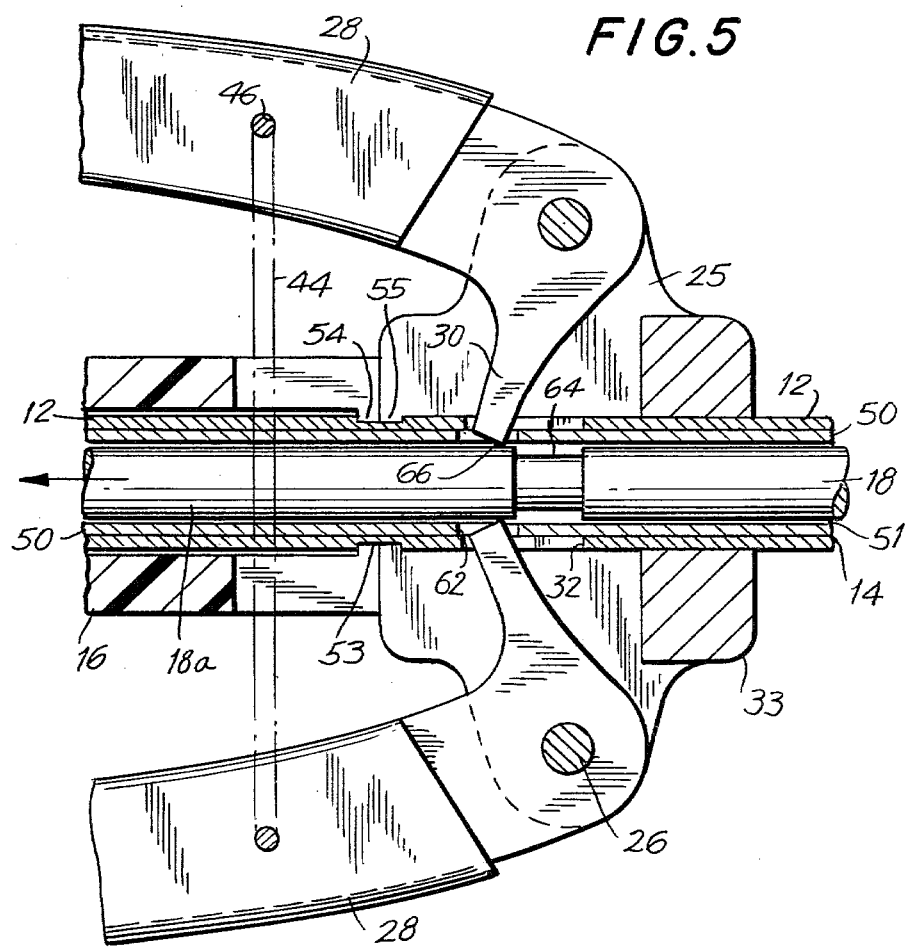
FIG. 5 is a fragmentary partial sectional view, similar to FIG. 2, of the housing, handles, pusher and central rod of the instrument of FIG. 1 when the central rod has been moved proximally, so that the anvil assembly and staple carrying assembly are close together but are still placed too far apart for fastening tissue.

As further seen from FIGS. 2, 5, 7 and 12, each second handle part 30 extends through one of the axial slots 31 in yoke 25, one of the axial slots 32 in the housing 12 and into one of the axial slots 62 in the pusher 50. As shown in FIGS. 2 and 5, when the proximal surface 40b of the stop screw 40 is not flush with, or proixmal of, the proximal surface 16a of the wing nut 16, the remote end 66 of each second handle part 30 abuts against the lateral surface 18a of the central rod 18, proximally of its groove 64, and cannot move distally and medially into the groove 64. As shown in FIGS. 7 and 12, only when the proximal surface 40b of the stop screw 40 is flush with, or proximal of, the proximal surface 16a of the wing nut 16 is the remote end 66 of each second handle part 30 free to move distally and medially into the groove 64 in the central rod 18 without abutting against the lateral surface 18a of the central rod 18, proximally of its groove 64. This is because the end 66 of each second handle part 30, remote from its pivot pin 26, is spaced from the pivot pin by a distance greater than the lateral distance from the pivot pin to the lateral surface 18a of the central rod 18.

When the remote end 66 of each second handle part 30 is free to move distally and medially into the groove 64 in the central rod 18 as shown in FIGS. 7 and 12, each second handle part 30 can move distally against the distal edge of one of the slots 62 in the pusher 50 to move the pusher distally. Distal movement of the pusher 50 causes the staple carrying assembly 22 to be activated, so that its staples 22A and knife 22B are urged distally against the pockets 20A and the knife cutting ring 20B, respectively, of the anvil assembly 20 and through tissue between the staple carrying assembly 22 and the anvil assembly 20 and its staples 22A are crimped by the pockets 20B of the anvil assembly.

The use of the instrument 10 of this invention in an anastomosis procedure is shown in FIGS. 1 to 15, particularly FIGS. 4, 10 and 15. After diseased tissue of a hollow organ 70 has been removed by conventional techniques, the distal end of the instrument 10 is inserted through a first hollow section 72 of the two sections of tissue 72 and 74 to be anastomosed (e.g., the instrument is inserted through the rectum in anastomosis of the large intestine using the rectal approach), so that only the anvil assembly 20 extends beyond the end of the first tissue section 72. The anvil assembly 20 is then moved distally of the staple carrying assembly 22 by rotating the wing nut 16. Rotating the wing nut 16 causes the central rod 18 to move distally through the bore 51 of the pusher 50 until the distal surface 40a of the stop screw 40 abuts against the annular shoulder 42 within the axial bore 17 of the wing nut 16. Rotation of the central rod 18 when rotating the wing nut 16 is prevented by the pairs of keys 36 on the staple carrying assembly 22 which slide within the axial keyways 34 in the central rod 18 as the central rod 18 moves distally.

As shown in FIG. 4, the end of the first section of tissue 72 is then fitted over the staple carrying assembly 22 and tied around the central rod 18 by a suture 75. The end of the second tissue section 74 is fitted over the anvil assembly 20 and tied around the central rod 18 by a suture 76.

As shown in FIG. 6, the wing nut 16 is then rotated again in the opposite direction to move the central rod 18 and the anvil assembly 20 thereon proximally until the proximal surface 40b of the stop screw 40 is flush with, or extends proximally of, the proximal surface 16a of the wing nut 16. Normally, the axial position of the central rod 18 relative to the housing 12 is such, when the proximal surface 40b of the stop screw 40 is flush with the proximal surface 16a of the wing nut 16, that the anvil assembly 20 and the staple carrying assembly 22 are properly spaced apart for fastening tissue between them. However, if a smaller space between the anvil and staple carrying assemblies 20 and 22 is desired (e.g., for fastening tissue that is somewhat thinner than normal), the wing nut 16 can be rotated further to move the central rod 18 and the anvil assembly 20 further proximally until the proximal surface 40b of the stop screw 40 is between the proximal and stepped surfaces 16a and 16b of the wing nut 16 or, as shown in FIG. 7, is flush with the stepped surface 16b of the wing nut 16.

When the desired spacing of the anvil and staple carrying assemblies 20 and 22 has been achieved, as indicated by the position of the proximal surface of the stop screw 40 in relation to the proximal and stepped surfaces 16a and 16b of the wing nut 16, the instrument 10 is ready to be used to fasten the tissue sections 72 and 74 with the staples 22A in the staple carrying assembly 22 as shown in FIG. 10.

As shown in FIGS. 11 and 12, the wire safety stop 44 is then removed from the holes 46 in the first handle parts 28. The handles 24 are then squeezed, so that the first handle parts 28 are urged towards the wing nut 16 and the housing 12. This causes the second handle parts 30 to rotate about the pivot pins 26 and to move distally and medially through the axial slots 31 in the yoke 25 and through the axial slots 32 in the housing 12. This also causes the second handle parts 30 to move: distally and medially through the axial slots 62 in the pusher 50; distally and medially into the axial groove 64 in the central rod 18; and distally against the distal edges of the slots 62 in the pusher 50 as shown in FIGS. 12 and 13. Such movement of the second handle parts 30 is without interference from any portions of the lateral surface 18a of the central rod 18, such as the portions proximal of its groove 64, and such movement can continue until the second handle parts 30 abut against the distal end of the groove 64 in the central rod 18. In this regard, squeezing the handles 24 causes each second handle part 30 to move medially and distally and to urge the distal edge of a slot 62 in the pusher 50 distally, to move the pusher 50 distally until the staple carrying assembly 22 is activated by the pusher 50 and until the staples 22A are urged distally against the pockets 20A of the anvil assembly 20 through the approximated sections of tissue 72 and 74, the staples 22A are crimped by the pockets 20A, and the portions of the sections of tissue 72 and 74 between the sutures 75 and 76 and the staples 22A are cut by the annular knife 22B and the knife cutting ring 20B as shown in FIG. 15.

In accordance with this invention, staples 22A are crimped by the pockets 20A of the anvil assembly 20 to the same extent, regardless of whether the proximal surface 40b of the stop screw 40 is flush with, or proximal of, the proximal surface 16a of the wing nut 16. This is because distal movement of the pusher 50, which serves to propel the staples 22A against the pockets 20A (i.e., distal movement of the pusher 50 into the staple carrying assembly 22), is the same whether the proximal surface 40b of the stop screw 40 is flush with, or proximal of, the proximal surface 16a of the wing nut 16. This feature permits the distal end of the groove 64 in the central rod 18 to be located, so that uniform proper crimping of the staples 22A can be obtained with the instrument 10, regardless of whether the proximal surface 40b of the stop screw 40 is flush with, or proximal of, the proximal surface 16a of the wing nut 16, in use.

After the sections of tissue 72 and 74 have been fastened by the staples 22A and cut by the knife 22B, the handles 24 are moved laterally away from the housing 12 and wing nut 16, so that the staple carrying assembly 22 and anvil assembly 20 can be separated to free the tissue between them. In this regard, the first handle parts 28 are moved laterally away from the housing 12, so that the second handle parts 30 rotate about the pivot pins 26 and move proximally and laterally out of the groove 64 in the central rod 18. Then, the handles 24 are held apart by replacing the stop wire lock 44 in the holes 46 in the first handle parts 28, and then the wing nut 16 is rotated again, as described above, to separate the anvil assembly 20 from the staple carrying assembly 22. Thereafter, the instrument 10 can be withdrawn from the fastened tissue sections 72 and 74. The excess tissue, cut away by the knife 22B of the staple carrying assembly 22, remains tied around the central rod 18 and can be removed and discarded with the instrument 10.

Figure 16:
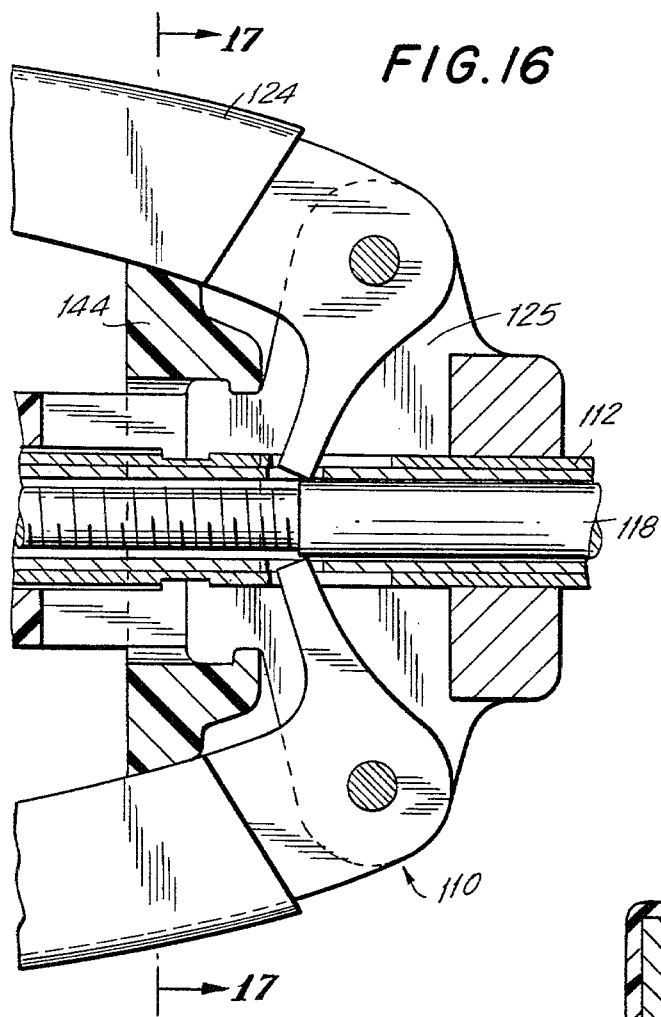
FIG. 16 is a partial sectional view, similar to FIG. 2, of an alternative embodiment of the surgical fastening instrument of this invention.
Figure 17:
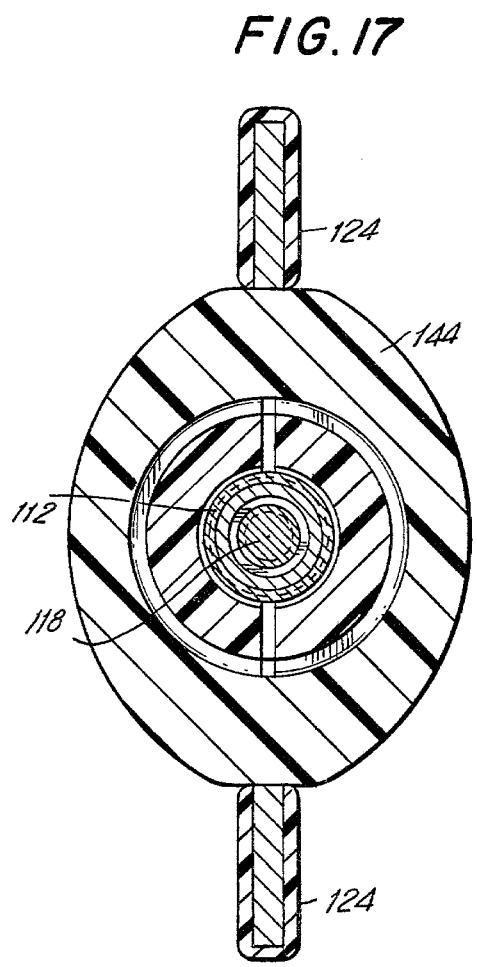
FIG. 17 is a sectional view, taken along line 17—17 in FIG. 16, showing the locking cam ring in locking position.
Figure 18:
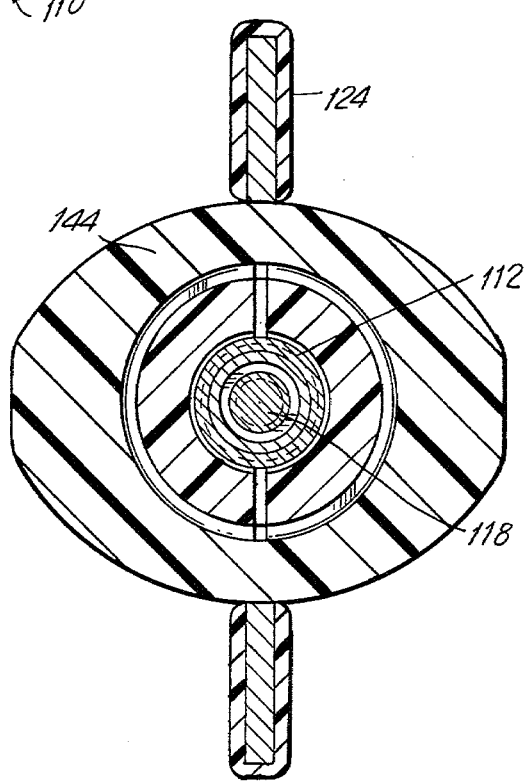
FIG. 18 is a sectional view, similar to FIG. 17, showing the locking cam ring when it is not in locking position and the handles have been moved towards the housing.

Shown in FIGS. 16 to 18 is another embodiment, generally 110, of the instrument for surgical fastening of this invention. In the instrument 110, elements corresponding to the elements of the instrument 10 of FIGS. 1 to 15 have reference numerals which differ by one hundred (100) from the elements of instrument 10 of FIGS. 1 to 15. In the instrument 110, the wire safety stop 44 of instrument 10 has been replaced by a locking cam ring 144. The locking cam ring is rotatably mounted about the axis of the housing 112 on the proximal end of the yoke 125 between the handles 124. As seen from FIGS. 17 and 18, the locking cam ring 144 has a generally elliptical shape about the axis of the housing 112, with the ends of its elliptical shape, at the ends of its major axis, being flat, so that such ends are parallel to its minor axis.

In operation, the locking cam ring 144 serves as an added safety feature to prevent the handles 124 from being moved medially towards the housing 112 of the instrument 110 until the distal end of the central rod 118 is located, relative to the distal end of the housing 112, so that the anvil and staple carrying assemblies of the instrument are properly spaced apart for fastening tissue between them. When the locking cam ring 144 has its major axis extending between the handles 124 as shown in FIG. 17, the flat ends of the locking cam ring 144 prevent the handles 124 from being moved medially towards the housing 112. When the locking cam ring 144 is rotated about the yoke 125, so that its minor axis extends between the handles 124, the handles can be moved medially towards the housing 112 without interference from the locking cam ring 144 as shown in FIG. 18.

It will be understood that the embodiments shown and described herein are merely illustrative of the principles of the invention and that various modifications can be made by those skilled in the art without departing from the spirit and scope of the invention, the forms hereinbefore described being merely preferred embodiments. In this regard, it is contemplated that all the parts of the instrument for surgical fastening of this invention could be made from metal. It is also contemplated that the housing, wing nut, central rod, pusher, and the bores of the housing and wing nut, as well as other elements of the instrument of this invention, could have cross-sections other than circular, such as square. It is further contemplated that only one handle or more than two handles could be used in the instrument of this invention.

I claim:

1. A surgical fastening instrument which comprises:
   (a) a tubular housing having an axial bore and an axial slot which extends through its tubular wall;
   (b) a tubular pusher axially located within the bore of said housing and adapted to move distally and proximally within the bore; said pusher having an axial slot extending through its tubular wall; said pusher slot being angularly aligned with said housing slot;
   (c) a central rod axially located within said pusher and adapted to move distally and proximally within said pusher; said central rod having an axial groove in its lateral surface; said central rod groove being angularly aligned with said pusher slot;
   (d) means, located at the proximal end of said housing, for moving said central rod distally and proximally within said pusher;
   (e) a handle pivotally mounted on the tubular wall of said housing; the pivotal mounting of said handle being laterally spaced from the tubular wall of said housing; a first part of said handle being located on the side of the pivotal mounting remote from said housing and being adapted to move about the pivotal mounting towards said housing; a second part of said handle being located on the other side of the pivotal mounting, adjacent to said housing, and being positioned within the slot in said housing and within the slot in said pusher; the second part of said handle being adapted to move distally against the distal end of the slot in said pusher to move said pusher distally within the bore of said housing upon movement of the first part of said handle towards said housing; the end of the second part of said handle, remote from the pivotal mounting, being spaced from the pivotal mounting by a distance greater than the lateral distance between the pivotal mounting and the lateral surface of said central rod;
   (f) an anvil mounted in a predetermined indexed orientation on the distal end of said central rod;
   (g) a staple carrying assembly mounted in a predetermined indexed orientation on the distal end of said housing between said anvil and the distal end of said pusher; said staple carrying assembly being activated by distal movement of said pusher against the proximal end of said staple carrying assembly, so that staples are urged distally against said anvil; and
   (h) means for determining that the axial position of the distal end of said central rod relative to the distal end of said housing is such that said anvil and said staple carrying member are properly spaced apart for fastening tissue between them;
   the groove in said central rod being located, so that when said anvil and said staple carrying assembly are properly spaced apart for fastening tissue between them: (1) at least a portion of the slot in said pusher is laterally aligned with at least a portion of the groove in said central rod; and (2) the end of the second part of said handle, remote from the pivotal mounting, can move medially and distally into the groove in said central rod and the second part of said handle can move distally against the distal end of the slot in said pusher to move said pusher distally within the bore of said housing against the proximal end of said staple carrying assembly to activate said staple carrying assembly.

2. The instrument of claim 1 wherein
   (1) the means for moving said central rod comprises:
      (a) threads on the lateral surface of a portion of said central rod adjacent its proximal end; and
      (b) a wing nut having an axial bore, a portion of which is threaded; the portion of said central rod, adjacent its proximal end, being located within the axial bore of said wing nut and the threaded lateral surface portion of said central rod being threadedly engaged with the threaded portion of the axial bore of said wing nut; and (2) wherein the means for determining that said anvil and said staple carrying assembly are properly spaced apart for fastening tissue between them comprises:

(a) a proximal end surface of said wing nut adjacent the axial bore in said wing nut;

(b) a stepped surface, projecting proximally from a portion of said wing nut proximal end surface, adjacent the axial bore in said wing nut; and (c) said central rod having a length such that (i) its proximal end is flush with the proximal end surface of said wing nut when said anvil and said staple carrying assembly are spaced apart by a maximum proper spacing, and (ii) its proximal end is flush with the stepped surface when said anvil and said staple carrying assembly are spaced apart by a minimum proper spacing.

3. The instrument of claim 1 wherein two of said handles are pivotally mounted on the tubular wall of said housing on diametrically opposite sides thereof so that the first parts of both handles fit within the grasp of one hand and so that the handles are operated by squeezing them together with one hand; said housing has two of said axial slots extending through its tubular wall on diametrically opposite sides thereof; said pusher has two of said axial slots extending through its tubular wall on diametrically opposite sides thereof; and said axial groove in the lateral surface of said central rod is a circumferential groove.

4. The instrument of claim 1 wherein the distal end of the groove in said central rod is located so that, when said anvil and said staple carrying assembly are properly spaced apart for fastening tissue between them, the second part of said handle can move distally against the distal end of the slot in said pusher to move said pusher distally to activate said staple carrying assembly, without the second part of said handle contacting the distal end of the groove in said central rod until after the staples of said staple carrying assembly have been properly crimped by said anvil, contact of said distal end of said central rod groove by the second part of said handle preventing further distal motion of said pusher by said handle.

5. A surgical fastening instrument which is adapted to have an anvil and a staple carrying assembly mounted in a predetermined indexed orientation on the instrument and which comprises:

(a) a tubular housing having an axial bore and two diametrically opposite axial slots which extend through its tubular wall; said housing being adapted to have the staple carrying assembly mounted on its distal end in the predetermined indexed orientation;

(b) a tubular pusher axially located within the bore of said housing and adapted to move (1) distally within the bore against the proximal end of a staple carrying assembly, when mounted on the distal end of said housing, to activate the staple carrying assembly and (2) proximally within the bore; said pusher having two diametrically opposite axial slots extending through its tubular wall; each pusher slot being angularly aligned with a respective one of said housing slots;

(c) a central rod axially located within said pusher and adapted to move distally and proximally within said pusher; said central rod having an axial groove in its lateral surface, portions of said groove being angularly aligned with each pusher slot; said central rod also being adapted to have the anvil mounted on its distal end in the predetermined indexed orientation, distally of the staple carrying assembly, when mounted on said central rod;

(d) means, located at the proximal end of said housing, for moving said central rod proximally and distally within said pusher;

(e) two substantially identical handles pivotally mounted on diametrically opposite sides of the tubular wall of said housing; the pivotal mounting of each handle being laterally spaced from the tubular wall of said housing; a first part of each handle being located on the side of the pivotal mounting remote from said housing and being adapted to move about the pivotal mounting towards said housing, the first parts of said handles being mutually spaced and adapted to fit within the grasp of one hand; a second part of each handle being located on the other side of the pivotal mounting, adjacent to said housing, and being positioned within a respective one of the slots in said housing and within the angularly aligned slot in said pusher; the second part of each handle being adapted to move distally against the distal end of the associated slot in said pusher to move said pusher distally within the bore of said housing upon movement of the first part of said handle towards said housing; the end of the second part of each handle, remote from the pivotal mounting, being spaced from the pivotal mounting by a distance greater than the lateral distance between the pivotal mounting and the lateral surface of said central rod; and (f) means for determining that the axial position of the distal end of said central rod relative to the distal end of said housing is such that the anvil, when mounted on the distal end of said central rod, and the staple carrying assembly, when mounted on the distal end of said housing, are properly spaced apart for fastening tissue between them;

the groove in said central rod being axially located, so that, when the anvil is mounted on the distal end of said central rod, the staple carrying assembly is mounted on the distal end of said housing and the anvil and the staple carrying assembly are properly spaced apart for fastening tissue between them: (1) at least a portion of each slot in said pusher is laterally aligned with at least a portion of the groove in said central rod; (2) the end of the second part of each handle, remote from the pivotal mounting, can move medially and distally into the groove of said central rod and the second part of said handle can move distally against the distal end of the associated slot of said pusher to move said pusher distally within the bore of said housing against the proximal end of the staple carrying assembly to activate the staple carrying assembly, so that staples are urged distally against the anvil; and (3) the end of the second part of each handle, remote from the pivotal mounting, can contact the distal end of the groove in said central rod only after said pusher has moved distally a sufficient distance to cause said staples to be properly crimped by said anvil, contact of said distal end of said central rod groove by said handles preventing further distal motion of said end of the second part of said handle and thereby preventing further distal motion of said pusher by said handles.

6. The instrument of claim 5 wherein
(1) the means for moving said central rod comprises:
  (a) threads on the lateral surface of a portion of said central rod adjacent its proximal end; and
  (b) a wing nut having an axial bore, a portion of which is threaded; the portion of said central rod, adjacent its proximal end, being located within the axial bore of said wing nut and the threaded lateral surface portion of said central rod being threadedly engaged with the threaded portion of the axial bore of said wing nut; and
(2) wherein the means for determining that said anvil and said staple carrying assembly are properly spaced apart for fastening tissue between them comprises:
  (a) a proximal end surface of said wing nut adjacent the axial bore in said wing nut;
  (b) a stepped surface, projecting proximally from a portion of said wing nut proximal end surface, adjacent the axial bore in said wing nut; and
  (c) said central rod having a length such that (i) its proximal end is flush with the proximal end surface of said wing nut when said anvil and said staple carrying assembly are spaced apart by a maximum proper spacing, and (ii) its proximal end is flush with the stepped surface when said anvil and said staple carrying assembly are spaced apart by a minimum proper spacing.

* * * * *

UNITED STATES PATENT AND TRADEMARK OFFICE
CERTIFICATE OF CORRECTION

PATENT NO. : 4,351,466
DATED : September 28, 1982
INVENTOR(S) : Douglas G. Noiles It is certified that error appears in the above—identified patent and that said Letters Patent is hereby corrected as shown below:

| Column | Line | | |
|--------|------|---|---|
| 2 | 59 | "handlers" should be | --handles-- |
| 3 | 6 | "placed" should be | --spaced-- |
| 4 | 60 | "stapling" should be | --staple-- |

Signed and Sealed this

Thirteenth Day of March 1984

[SEAL]

Attest:

Attesting Officer

GERALD J. MOSSINGHOFF

Commissioner of Patents and Trademarks